US009103762B2

(12) United States Patent
Kohler et al.

(10) Patent No.: US 9,103,762 B2
(45) Date of Patent: Aug. 11, 2015

(54) METHOD FOR ELECTRICAL DETECTION OF BIOMOLECULES BY METAL DISSOLUTION AND ASSAY KIT THEREFORE

(75) Inventors: Fabian Kohler, Rheinfelden (DE); Robert Grass, Zurich (CH); Wendelin Jan Stark, Zurich (CH)

(73) Assignee: ETH Zurich, Zurich (CH)

( * ) Notice: Subject to any disclaimer, the term of this patent is extended or adjusted under 35 U.S.C. 154(b) by 250 days.

(21) Appl. No.: 13/881,742

(22) PCT Filed: Oct. 26, 2011

(86) PCT No.: PCT/CH2011/000263
§ 371 (c)(1),
(2), (4) Date: Apr. 26, 2013

(87) PCT Pub. No.: WO2012/055060
PCT Pub. Date: May 3, 2012

(65) Prior Publication Data
US 2013/0302832 A1    Nov. 14, 2013

(30) Foreign Application Priority Data
Oct. 28, 2010 (EP) .................................. 10014071

(51) Int. Cl.
*G01N 27/00* (2006.01)
*C12Q 1/00* (2006.01)
*G01N 33/543* (2006.01)
*G01N 33/58* (2006.01)
*G01N 27/04* (2006.01)

(52) U.S. Cl.
CPC ................ *G01N 27/00* (2013.01); *C12Q 1/001* (2013.01); *G01N 27/041* (2013.01); *G01N 33/54373* (2013.01); *G01N 33/581* (2013.01)

(58) Field of Classification Search
CPC ..... G01N 27/00; G01N 33/581; G01N 27/041; G01N 33/54373; C12Q 1/001
See application file for complete search history.

(56) References Cited

U.S. PATENT DOCUMENTS

| | | |
|---|---|---|
| 3,595,755 A | 7/1971 | Hartel |
| 4,830,959 A | 5/1989 | McNeil et al. |
| 5,166,054 A | 11/1992 | Naqui |
| 5,296,125 A | 3/1994 | Glass et al. |
| 5,338,708 A * | 8/1994 | Felten ............................ 501/19 |
| 5,820,746 A * | 10/1998 | Kawaguchi et al. .......... 205/791 |
| 2002/0106290 A1 | 8/2002 | Bader et al. |

(Continued)

FOREIGN PATENT DOCUMENTS

| | | |
|---|---|---|
| EP | 0 136 362 A1 | 4/1985 |
| GB | 843 028 | 8/1960 |
| WO | 2008/109617 A1 | 9/2008 |

OTHER PUBLICATIONS

International Search Report for corresponding International Application No. PCT/CH2011/000263 dated Mar. 2, 2012.
Abdel-Hamid et al., "Development of a flow-through immunoassay system", Sensors and Actuators B, vol. 49, 1998, pp. 202-210.
Warsinke et al., "Electrochemical immunoassays", Fresenius Journal of Analytical Chemistry, vol. 366, 2000, pp. 622-634.

(Continued)

*Primary Examiner* — Melanie Y Brown
(74) *Attorney, Agent, or Firm* — Renner, Otto, Boisselle & Sklar, LLP (57) ABSTRACT

The present invention relates to a method for detecting a target molecule in a sample by metal dissolution as described in the specification, said method using an electrical readout; to kits adapted for this method and to electrodes suitable for such kits and methods.

7 Claims, 3 Drawing Sheets

(56) References Cited

U.S. PATENT DOCUMENTS

| | | |
|---|---|---|
| 2003/0186274 A1 | 10/2003 | Limoges et al. |
| 2004/0265922 A1 | 12/2004 | Bieniarz et al. |
| 2006/0097982 A1* | 5/2006 | Arai et al. .................... 345/105 |
| 2007/0231794 A1 | 10/2007 | Dill et al. |
| 2010/0105566 A1 | 4/2010 | Bieniarz et al. |
| 2010/0209521 A1* | 8/2010 | Schalkhammer ............. 424/497 |
| 2011/0050259 A1* | 3/2011 | Wilson ........................ 324/700 |
| 2011/0315962 A1 | 12/2011 | Lieber et al. |
| 2013/0217124 A1* | 8/2013 | Mirkin et al. ................ 435/375 |

OTHER PUBLICATIONS

Ramgir et al., "Nanowire-Based Sensors", Small, vol. 6, No. 16, 2010, pp. 1705-1722.

Bruchertseifer et al., "Analysis of iodine species in aqueous solutions", Anal Bioanal Chem, vol. 375, 2003, pp. 1107-1110.

Stark et al., "Investigation of the IC-ICP-MS determination of iodine species with reference to sample digestion procedures", Fresenius Journal of Analytical Chemistry, vol. 359, 1997, pp. 371-374.

* cited by examiner

METHOD FOR ELECTRICAL DETECTION OF BIOMOLECULES BY METAL DISSOLUTION AND ASSAY KIT THEREFORE

This application is a national phase of International Application No. PCT/CH2011/000263 filed Oct. 26, 2011, and published in the English language which claims priority to EP 10014071.4 filed Oct. 28, 2010.

The present invention relates to a method for detecting a target biomolecule in a sample by metal dissolution, said method using an electrical readout; to kits adapted for this method and to electrodes suitable for such kits and methods.

Medical diagnostics, biomedical research and molecular biology make use of a field of detection technologies where a large range of most different methods target the analysis of small concentrations of clinically relevant molecules, intermediates, proteins and other entities ("target molecules"). Among the existing approaches for detecting the target molecule, most systems use optical techniques to detect these entities. For example ELISA (enzyme linked immunosorbent assay)-type assays offer a versatile technology platform enabling the analysis of tens of thousands of target molecules. Such assays make use of specific interactions between a substrate and an antibody or other target recognizing entities. The molecules are detected as enzymes attached to the target recognizing entities produce colored products. Other optical methods use dyes or fluorescent molecules which allow a direct optical readout. Assays giving a qualitative answer (Yes/No) typically rely on the coloration or color change. Said methods are often used in rapid home tests or point of care tests. Given the often small concentrations of the investigated molecules, all assays require a reliable technique to detect an event. Amplification can be necessary over many orders of magnitude. Various detection systems are known, which generally allow marking a target molecule and measure its concentration within a small area of interest using e.g. absorption effects, fluorescence effects, radioactive effects, magnetic effects.

Optical Readout Using Absorption.

In this set up, either a dye (a highly absorbing molecule) is linked to the detection antibody/target specific entity, or an enzyme is linked to the detection antibody/target specific entity and converts an additional substrate into an absorbing form. The most prominent example there is horse radish peroxidase (HRP), which catalyses the oxidation of chromogenic substrates like 3,3',5,5'-tetramethylbenzidine (TMP) to a colored product. Another enzyme is alkaline phosphatase capable of dephosphorylating chromogenic substrates, which change their colour or become colored molecules after dephosphorylation.

Optical Readout Using Fluorescence.

In this set up, a fluorophore is linked to the detection antibody/target specific entity. The fluorophore is excited at a specific wavelength of light and relaxes by releasing light of a different wavelength, which is detected with an optical sensor.

Radioimmunoassays.

These assays use radioactive antigens (hot) bound to antibodies. Upon adding a liquid containing an unknown amount of non radioactive antigens (cold), both antigens (hot and cold) compete for the antigen specific antibody and part of the hot antigen is released. Measuring the amount of released hot antigens (radioactive) by a gamma counter the amount of cold antigen is calculated. The disadvantage of this detection technique is the employment of radioactivity itself that demands special precautions, specialized working places and controlled waste treatment. In addition, the radioactive labeling of antigens is expensive.

Readout Using Magnetic Effects.

These assays are based on magnetic detection; a change of magnetization or magnetic susceptibility upon binding of target molecules is detected.

Further, a number of specific assays and devices for detecting biomolecules are known:

Hainfeld et al (WO 2008/109617) discloses an enzymatic assay for the detection of target molecules in a sample. The target molecule is bound by a capturing molecule which in turn is linked to an enzyme. Upon incubation with metal ions, an oxidizing agent and a reducing agent, the metal ions are reduced to elemental metal which is deposited. The degree of metal deposition is subsequently measured as indicator for the absence or presence of the target molecule. This method has however the drawback that in the case of small concentrations no change in electrical signal (conductance or resistance) is measurable. The deposited metal is not percolating in the beginning and only at a certain threshold concentration or incubation time starts percolating and therefore becomes conducting. As the measured signal is typically rather small, it needs to be amplified by a second metal deposition step, which uses the enzymatically deposited metal particles as seeds for the growth of larger metal agglomerates. This procedure helps to start percolating metal structures, which are necessary for the electrical measurement.

Abdel Hamid et al (Sensors and Actuators B49, 1998, 202ff.) disclose a flow-through immunoassay system comprising an amperometric immunosensor. A sample liquid comprising the target molecule is flown through an immunocolumn comprising antibodies specific for the target molecule. Then, peroxidase-labeled antibodies are added which bind to target molecules bound to the antibodies within the column material, thereby building a complex. Subsequently, peroxide and iodide are added such that the peroxidase activity oxidizes the iodide. Finally, an amperometric output is measured. The used set-up relies on amperometric signals, which are essentially voltage differences within liquids. Therefore the system needs several electrodes for the measurement, a reference electrode, at least one electrode with a permanently applied test voltage and at least one measurement electrode. This setup is known from standard blood glucose meters and can handle normally only a small analyte concentration range. In general, amperometric measurements rely on the change of chemical potential by a chemical or enzymatic reaction.

Warsinke et al (Fresenius J Anal. Chem. 2000, 366, 622 ff) offer a review of different amperometric and potentiometric electrochemical immunoassays.

Ramgir et al (small 2010, 6, 16, 1705 ff) discuss nanowire-based sensors in general, its manufacturing, sensitization mechanisms and applications. To the extend metallic sensors are disclosed, they have a weight of 5 pg or less. Further, such sensors comprise immobilized molecules on top of the metallic nanowires.

In summary, diagnostic and molecular biology research relies mainly on ELISA systems and the associated optical systems ("the measuring devices"). Such optical systems have remained quite expensive, are quite large and are found in specialized diagnostic laboratories or in research facilities.

In consequence, there is an ever existing need for alternative or improved test assays, associated methods and measuring devices.

Thus, it is an object of the present invention to mitigate at least some of these drawbacks of the state of the art. In particular, it is an aim of the present invention to provide improved detection systems, in particular for immunoassays. Particularly there is a need for systems being less expensive, smaller, and more convenient in use.

These objectives are achieved by a method as defined in claim 1, an electrode as defined in claim 10 and a kit as defined in claim 6. Further aspects of the invention are disclosed in the specification and independent claims, preferred embodiments are disclosed in the specification and the dependent claims.

The present invention provides direct and indirect detection systems for target molecules in a sample. Up to now, such direct detection systems are found in lateral flow devices using optical detection by colour change, where one can read or visually see the result.

The present invention utilizes the fact that electrical properties of the electrode described herein depend on the cross section, length of the wire and the behavior of the electrode towards changes in the chemical composition. Consider the electrical resistance; if the metal stripe height is halved, the resistance of that stripe is doubled. If the stripe is entirely removed, the resistance is infinite (i.e. the electrical connection is broken).

The present invention will be described in more detail below. It is understood that the various embodiments, preferences and ranges as provided/disclosed in this specification may be combined at will. Further, depending of the specific embodiment, selected definitions, embodiments or ranges may not apply.

Unless otherwise stated, the following definitions shall apply in this specification:

The term "reaction chamber" refers to a 2D area (e.g. a surface) or a 3D area (e.g. vessel) where the inventive method takes place. Suitable reaction chambers include chambers adapted for static samples (such as microplates having e.g. 6, 12, 24, 96, 384 or 1536 sample wells) and chamber adapted for flowing samples (such as a microfluidic device or a strip).

The term "electrical property" refers to an electrical property generated or changed which can be measured; it includes resistance, and/or conductivity, e.g. detectable between the connector areas of an electrode.

The term "biomolecule" refers to any molecule existing in nature or artificially synthesized according to a matrix existing in nature, and comprises for example antibodies, proteins, peptides, nucleic acid sequences, i.e. oligonucleotides comprising at least two deoxyribonucleotides or ribonucleotides, optionally comprising at least one modified nucleotide for example a nucleotide containing a modified base, hormone receptors, lipids, antigens.

The term "polypeptide" as used herein refers to any peptide of at least two amino acids in particular a protein, a protein fragment or oligopeptide. A protein or protein fragment may have a biochemical activity, such as en enzyme or an antibody, or be a structural protein.

The term "nucleic acid sequence" refers to any oligonucleotides comprising at least 5 deoxyribonucleotide or ribonucleotide units. The term thus comprises DNA, RNA, LNA, PNA and chimeras thereof. The nucleic acid sequence may be single or double stranded.

The term "support" denotes any solid three-dimensional body, which does not chemically or physically interact with a sample.

The term "complex" refers to an entity formed by at least two different molecular entities, interacting by van der Waals interactions, hydrogen bonds or other interactions. Typically, covalent bonds are not involved the complex formation as used herein.

The present invention will be better understood by reference to the figures.

20—Support
21—Reporter Enzyme (Prior art)
22—Reporter Enzyme (This invention)
23—Substrate (Prior art)
24—Enzyme product (Prior art)
25—Light emitter
26—Light detector
27—Electrical property
28—Substrate (This invention)
29—Enzyme Product (This invention)
30—Primary antibody
31—Target molecule
32—Detection antibody or Secondary antibody
33—Conjugation between secondary antibody (32) and reporter enzyme (21/22).

11—Connector area
12—Metal wire
13—Contact area.

In more general terms, in a first aspect, the invention relates to a method for detecting a target molecule in a sample by measuring an electrical property such as conductivity and/or resistance, whereby said property is affected by the dissolution of an electrode due to the presence of said target molecule in said sample, whereby said target molecule is bound to an enzyme-labelled detection biomolecule and whereby said enzyme catalyses a reaction which forms a reactive species which dissolves metals. The inventive method therefore combines the following elements to detect (i.e. qualitatively and/or quantitatively determine) a target molecule: First, an enzyme catalyzed production of a reactive species; second, dissolution of a metal by said reactive species; third, measuring an electrical property altered by metal dissolution.

Particularly, the invention relates to a method for detecting a target molecule in a sample comprising binding an enzyme-labelled detection biomolecule to the target molecule in the presence an inactivated metal dissolving species, thereby activating said species and facilitating metal dissolution. The detection biomolecule is typically an enzyme-conjugate which binds specifically to the target molecule. The enzyme catalyzes a reaction which produces a reactive species, which by itself or by a decomposition product of said species enhances the dissolution of metals. A wire of said metal is brought in contact with the solution containing said analyte, enzyme-conjugate and/or said reactive species. Measuring the conductivity or resistivity of said wire allows detecting and/or quantifying said analyte.

In a preferred embodiment, the invention relates to a method for detecting a target molecule 31 in a sample by means of a metal wire, said method comprising the steps of:

a) providing a detection biomolecule 32 interacting with the target molecule 31, wherein said detection biomolecule is linked to an enzyme 22;
b) contacting the sample with the detection biomolecule 32, thereby the detection biomolecule 32 and the target molecule 31 interacting together 33;
c) separating non-interacting and interacting detection biomolecules;
d) adding a substrate 28 of the enzyme 22;
e) transforming the substrate 28 by enzymatic catalysis into a product 29, wherein said product 29 is a reactive species dissolving metal of the wire, thereby altering the conductivity of the wire; and
f) measuring the conductivity/resistance of the wire.

Typically, the reaction is performed in a reaction chamber. The invention is not limited to a specific reaction chamber. Suitable reaction chambers are microplates having multiple wells, e.g. 6, 12, 24, 96, 384 or 1536 sample wells. Alternatively, the reaction chamber may be a chip or a strip. The reaction chamber, for example a chip or a strip, may be adapted for flow-through fluidics; alternatively, the reaction chamber may be adapted for a batch-wise assay. The reaction mixture is typically a liquid; usually, the reaction takes place under oxidizing conditions, but may also be adapted for slightly reducing conditions. The assay may be directly run in a reaction chamber or the corresponding liquid volume from the assay is transferred into a reaction chamber for detection. The reaction chamber has a small volume where the liquid can access at least one inventive wire made from a suitable metal/metal oxide.

The sample is preferably a biological sample, such as, but without being limited to, blood, blood serum, lymph, urine, pancreatic juices, bile, tear fluid or saliva.

The target molecule 31 for which the sample is analyzed may be a chemical entity ("small molecule"), a polypeptide (such as an antigen, an antibody, an enzyme), or a nucleic acid sequence (DNA or RNA), or an oligo- or polysaccharide. In one embodiment, the chemical entity is a sugar derivative. The target nucleic acid sequence may be double stranded DNA, single stranded DNA, a DNA-RNA hybrid or RNA (ribosomal or messenger). Typically, in case of double stranded or hybrid nucleic acid sequences, the nucleic acid sequence is denatured before carrying out the instant method.

The detection biomolecule 32 is preferably an antibody or a nucleic acid sequence comprising at least a segment being complementary to the target nucleic acid sequence. It is well known to the skilled person that antibodies interact with, and preferably bind to, even more preferably bind specifically to, target molecules having the corresponding recognition epitope, such as polypeptides, proteins, nucleic acids, but also chemical entities.

Figure 1:
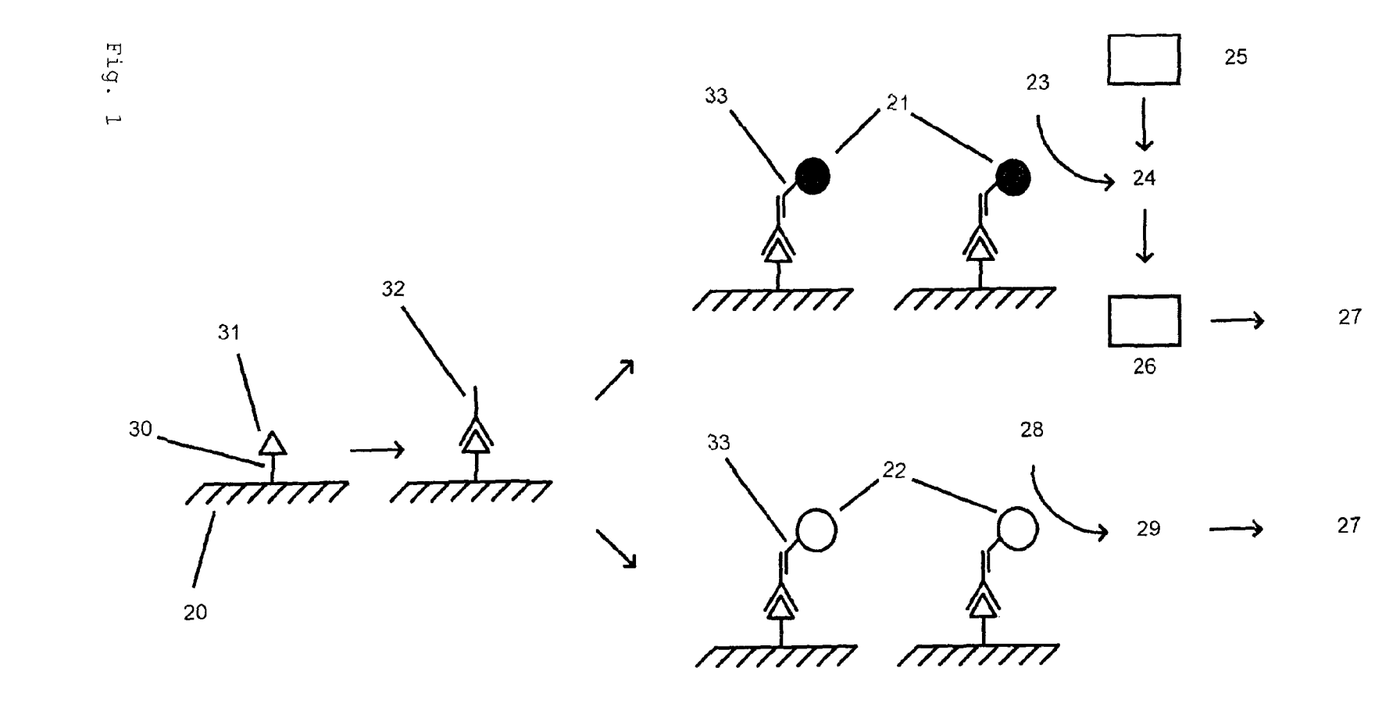
FIG. 1 shows a schematic overview of the differences between standard sandwich ELISA for detecting a target biomolecule using optical detection methods and a sandwich ELISA adapted according to the present method for detecting a target molecule using an electrical property. In this figure, the references are as follows.

In one embodiment of the method disclosed herein, the target molecule 31 binds to a capturing biomolecule 30 and is then recognized by the detecting biomolecule 32. This is e.g. the case in a sandwich ELISA as depicted in FIG. 1. Such a capturing biomolecule 30 may e.g. be an antibody if the target molecule 31 is a polypeptide, a nucleic acid sequence or a chemical entity; an antigen if the target molecule is an antibody or other biomolecule being able to bind to the antigen; or a nucleic acid sequence comprising a segment which is at least partially complementary to the target nucleic acid sequence 31. The capturing biomolecule 30 is preferably immobilized on a solid support 20, e.g. on a surface of the reaction chamber.

For purposes herein, the detection biomolecule 32 is linked or conjugated to an enzyme 22. Said conjugation is preferably a covalent linkage, but may well be another suitable linkage, like a biotin avidin or streptavidin conjugate.

The target molecule 31 and the detection biomolecule 32 are brought in contact so that specific interaction between both occurs. Thereby, a capture complex 33 is formed. Usually, a non-covalent bond, such as a hydrogen bond or van der Waals interactions are formed between the target molecule and the detection biomolecule 32. The capture complex 33 will only form if there is an affinity of the detection biomolecule 32 and the target molecule 31, including, but not limited to, antibody-antigen interaction or complementary base pairing of nucleic acid sequences.

In a subsequent step, those detection biomolecules 32 which do not interact with a target molecule 31 are separated from the capture complexes 33. Otherwise, a signal would be measured although the target molecule 31 of interest is not present. In a preferred embodiment of the instant method, non-interacting detection biomolecules 32 are removed from the reaction chamber.

Subsequently, the substrate 28 of the enzyme is added to the interaction complex of target and detection biomolecule. Enzymes typically display a wide variety with respect to their chemical nature, structure and reactions to be catalyzed. Therefore, they can be tailored and selected according to the specific needs. For the instant method, it is necessary that a product is formed which is able to dissolve directly or indirectly a metal wire. Preferably, the enzyme is selected from the group consisting of: hydrolases (in particular hydroxynitrile lyases, oxynitrilases), glucosidases, peroxidases, esterases, etherases, sulfurtransferases, sulphur transferases and desulfohydrolases. Although enzymes are widely known in the art, the use of enzymes to dissolve metals has until know not been shown directly. The invention thus relates to the use of enzymes, particularly to the enzymes defined above, (a) for dissolving metals (particularly as defined herein) and (b) for measuring an electrical property of the metal which is altered through its dissolution (particularly as defined herein).

The substrate 28 is typically selected specifically for the enzyme 22. Preferably, the substrate 28 is selected from the group consisting of cyanogenic glycosides, cyanogenic lipids, cyanide, hydrogen peroxide, thiosulfate, esters or ethers of alpha hydroxynitriles, iodide, chloride, bromide, or biomolecules comprising a iodide, chloride or bromide group. Much preferred are cyanogenic glycosides.

Typically, said substrate 28 is provided in a buffer solution. Additionally, one or more additives may be in the solution: coenzymes (such as NAD, FAD or hydrogen peroxide), surfactans (such as TWEEN, sodium dodecylsulfate, 3-(N-morpholino)propanesulfonic acid), preserving agents, accelerators, active metal dissolving species. The additional use of an active metal dissolving species is particularly advantageous for indirect assays wherein the active metal dissolving species is consumed; upon its consumption by the enzyme reaction, its concentration is reduced in the reaction mixture.

The dissolution of metals is well understood. In particular, the dissolution of gold is well investigated; numerous approaches can be used to accelerate the gold dissolution. One of several factors in the dissolution process is the abundance of oxidants, which can be increased by the addition of peroxide derivative (such as hydrogen peroxide, organic peroxides (such as tert-butyl hydroperoxide, peroxy acids)) or by increasing the dissolved oxygen content. Alternatively or additionally, the addition of heavy metal ions the reaction (such as bismuth, thallium, mercury, lead) can be accelerated as well. Consequently, the invention further provides a method as described herein, wherein in step d) or e) a peroxide derivative and/or a compound comprising heavy metal ions is added.

Optionally, the active metal dissolving species may be regenerated by adding reducing agents which do not interfere with the measurement itself, the measurement time is shortened as more active metal dissolving species are available for detection.

In one embodiment of the method of the invention, the enzyme 22 will catalyze the reaction and liberate from the substrate 28 a product 29 which is a reactive species able to dissolve the metal of the wire. Said reactive species 29 is typically a soluble product. Preferably, the reactive species 29 is cyanide, cyanohydrin, hypochlorite, hypobromites, iodine, triiodide, thiocyanate. Much preferred is cyanide. The reactive species 29 may also be an intermediate compound that by itself or catalytically generates cyanide ions, oxidizes halogenides, generates thiocyanates or generates sulfides. Examples thereof include alpha hydroxynitriles which decompose to cyanides.

There are many enzyme-substrate combinations useful in the present invention. The following combinations are preferred:

The enzyme being a glucosidase, preferably a beta-D-glucosidase, more preferably linamarase, amygdalase, prunasin beta-glucosidase; and the substrate being a cyanogenic glycoside. The enzyme reaction generates an alpha-hydroxynitrile which decomposes to cyanide. Said enzyme-substrate combination is particularly advantageous for wires consisting of gold, platin group metals or silver (and/or combinations thereof and/or alloys).

The enzyme being a peroxidase, preferably a haloperoxidase, more preferably iodoperoxidase, bromoperoxidase or lactoperoxidase; and the substrate being iodide or bromide or a molecule having a iodide or bromide group. The enzyme reaction generates iodine or hypobromite, respectively. Said enzyme-substrate combination is particularly advantageous for wires consisting of gold, platinum, palladium, rhodium and/or combinations thereof and/or alloys)

The enzyme being a hydrolase, preferably alpha hydroxylnitrilase, mandelonitrile lyase, oxynitrilase; and the substrate being alpha hydroxynitrile or mandelonitrile. The enzyme reaction of all pairs generates cyanide. Said enzyme-substrate combination is particularly advantageous for wires consisting of gold, platin group metals or silver (and/or combinations thereof and/or alloys).

Another example is glycine dehydrogenase which catalyzes the decomposition of glycine derivatives into cyanide and organic molecules. The hydrolase-substrate combination is particularly advantageous for wires consisting of gold, platin group metals or silver (and/or combinations thereof and or/alloys thereof).

The enzyme being a sulfurtransferase, preferably a rhodanese and the substrate being either cyanide or thiosulfate. The enzyme reaction generates thiocyanate or sulphite, respectively. Said enzyme-substrate combination is particularly advantageous for wires consisting of gold or silver and/or combinations thereof and/or alloys thereof. In another embodiment, the sulfurtransferase is a sulphite reductase, using sulphite as substrate. The according enzyme reaction generates sulphide which preferably dissolves gold wires and/or combinations thereof and/or alloys thereof. In another embodiment, the sulfurtransferase is a sulphur reductase, using sulphur or polysulfide as a substrate; the reactive species generated from both substrates is sulphide. Again, this combination is particularly useful for dissolving gold wires and/or alloys thereof.

The enzyme being a cystein synthase, a nitrilase, or a nitrilhydratase and the substrate being cyanide. The enzyme reaction consumes cyanide. Said enzyme-substrate combination is particularly advantageous for wires consisting of gold or silver and/or combinations thereof and/or alloys thereof.

The enzyme being an esterase, preferably a lipase; and the substrate being esters of alpha hydroxynitriles (such as cyanogenic lipids). The enzyme reaction generates alpha hydroxynitriles, which decompose to cyanide. Said enzyme-substrate combination is particularly advantageous for wires consisting of gold, platin group metals or silver and/or combinations thereof and/or alloys thereof.

The enzyme being an etherase and the substrate being an ether of alpha hydroxynitriles. The enzyme reaction generates alpha hydroxynitriles, which decompose to cyanide. Said enzyme-substrate combination is particularly advantageous for wires consisting of gold, platin group metals or silver and/or combinations thereof and/or alloys thereof.

In a preferred embodiment of the method disclosed herein, the method uses an enzyme substrate combination consisting of an esterase and a cyanogenic ester. In this embodiment, the cyanogenic ester is hydrolyzed by said enzyme into a carboxylic acid and an alpha hydroxynitrile, which decomposes by itself as it is unstable or is decomposed by the action of hydroxynitrilases to cyanide ions. The cyanide ions are measured using the wire described herein.

The metal wire may be comprised within the reaction chamber or may be provided in a separate step to the reaction mixture. It may thus be present before or after the substrate of the enzyme is added. Also, part of the method may take place in one reaction chamber and the reaction mixture is then transferred to another reaction chamber comprising the metal wire. Further, (i) the inventive wire can be immersed in the reaction mixture (for example in assay plates) or (ii) the reaction mixture is dropped onto the inventive wire (for example in test stripes) or (iii) the reaction mixture is passed over the inventive wire (for example in microfluidic devices).

Particularly suitable are metal wires as defined below. The term "wire" as used herein comprises wires, metal stripes and metal electrodes, in particular those described herein. In a preferred embodiment, the wire has a weight of at least about 10 pg and up to about 100 µg. Through the dissolution of metal of the wire, the conductivity of the wire, respectively its resistance, is altered. Thus, the change (i.e. decrease/increase) of the electrical property is indicative of the presence of the target molecule.

Preferably, the electrical property is measured as resistivity which increases or as conductivity/current which decreases, when compared to a control wire. Alternatively, the value for the electrical conductivity obtained in step f) is compared with a value obtained before step d).

The change in electrical conductivity may e.g. be measured by a method selected from the group consisting of (without being limited to) amperometric measurements, differential pulse voltammetry, chronoamperometry, impedance measurements, potentiometric measurements.

The change in electrical resistivity may e.g. be measured by a method selected from the group consisting of (without being limited to) amperometric measurements, differential pulse voltammetry, chronoamperometry, impedance measurements, potentiometric measurements.

The present method is not limited to a specific assay format. The present method is thus suitable for various assays for detecting target molecules, e.g. immunoassays, in situ histochemical assays, or DNA-, RNA microarray techniques. In one embodiment, the method described herein relates to a direct enzyme linked immunosorbent assay (ELISA) assay.

For example, a direct ELISA assay may be modified in general terms that the target interacts specifically with an enzyme-conjugate. After wash off excess enzyme-conjugate, the reaction chamber is fed a solution containing a substrate for said enzyme. The substrate is in the form of an inactivated metal dissolution chemical species. The enzyme catalyses the reaction of said substrate to an activated species. Said activated species can directly dissolve suitable metals or is a species which decomposes to a metal dissolving species by itself or the action of suitable catalysts/chemicals or enzymes. If the reaction chamber of this modified ELISA assay contains a thin wire of a suitable metal, said activated species will affect the metal wire by formation of soluble metal ions or metal ion complexes. This dissolution changes the electrical resistance of the metal wire. This change in electrical resistance can directly be read-out by a conventional electrical circuitry or device. In addition the fact that thin metal stripes are visible by eye or small lenses makes an optical control applicable. Changing amounts of enzyme results in altered concentrations of activated species and altered metal wire dissolution. As a consequence, the altered amount of enzyme (corresponding to an altered amount of target in the tested sample) is translated into an altered electrical resistance change in time which by itself is a readable signal.

In a specific embodiment thereof, a direct ELISA may be performed as follows: The method is performed as above; and the enzyme is a beta-d-glucosidase like linamarase. After linking and washing off excess of unbound linamarase, a cyanogenic glycoside like linamarin is given to the assay and converted through the action of linamarase to an alpha-hydroxynitrile (here acetone cyanohydrin) which decomposes above pH 5 or can be decomposed by a alpha-hydroxynitrilase to cyanide and acetone. The produced cyanide dissolves metals (e.g. gold, gold alloys, silver, silver alloys, noble metal alloys or platin group metals (PGM)) and changes electrical resistance of the metal wire.

In another specific embodiment thereof, the enzyme of the detection biomolecule is a peroxidase, preferably a haloperoxidase, most preferably an iodoperoxidase. After the specific interaction of target and detection molecule took place, excess unbound peroxidase is washed off, halide ions (preferably iodide) are given to the assay in the form of metal salts or sources of halide ions and converted through the action of the peroxidase to iodine. The iodine dissolves metals (e.g. gold, gold alloys, silver, silver alloys, noble metal alloys or platin group metals (PGM)) and changes electrical resistance of the metal wire.

In an exemplary embodiment, the complete analysis is conducted in the following steps. A 96-well plate coated with human C-reactive protein (CRP) is blocked by incubation with BSA solution. After washing the wells, serum, whole blood, saliva, urine or any kind of sample fluid, preferably as aqueous buffered solution, is incubated in the wells. After an additional washing step, the streptavidin modified CRP detection antibody is added and allowed to bind to immobilized CRP in the wells. After washing, the biotinylated beta-glucosidase is added and allowed to bind to the immobilized streptavidin modified antibody. After washing, a substrate solution containing a substrate of the biotinylated enzyme is added and allowed to react with the enzyme for a defined time, preferably 1-30 minutes, most preferably 2-10 minutes, even more preferably between 5-7 minutes. The substrate incubation is carried out between 17 and 55° C., for linamarase from cassava the preferred temperature range is between 20° C. and 45° C. After addition of a stop solution containing 0.01M to 2M Sodium hydroxide and 0.1 mg/l to 50 mg/l bismuth nitrate or more preferably Thallium nitrate. At this point, the gold wire (sensor) is inserted into the solution and the resistance is measured in a 4 point setup using a constant applied bias of 0.1 to 1000 mV, preferably 1 to 100 mV, most preferably 2 to 10 mV. The resistance is monitored until a steady increase is obvious. After this, the slope of the resistance versus time is extracted and compared to a reference value. This leads to the corresponding concentration of CRP in the test solution.

If a diagnostic or research protocol only asks for the presence or absence of a target molecule in a given concentration range (qualitative detection), the method described herein can be performed as follows: The enzyme and substrate are allowed to release the active metal dissolving species, i.e. the reactive species, action during a given time (e.g. the assay delay time), the wire is then tested for electrical conductance and can either be broken (no conductivity) or conducting. Thereby, a yes/no answer giving a "green/red" type of overall answer is generated. No specific fine measurements on the resistance are necessary. The conditions of the assay are adapted for the needs of the diagnostic or research protocol. The invention thus provides a method as described herein for qualitatively detect a target molecule.

In another embodiment, the method described herein may be adapted for a concentration dependent assay (quantitative detection). Since a change in a metal wire dimension (overall metal cross section) depends on the concentration of the reactive species such as e.g. cyanide, and later depends on the amount of enzyme releasing the active species, the amount of target can be linked to the change in electrical conductivity or resistance. This concentration dependent effect allows distinguishing different target molecule concentrations and gives diagnostically more valuable information than the above described Yes/No answer. The invention thus provides a method as described herein for quantitatively detect a target molecule.

The advantage of the method described herein is that the setups do not require an optical unit. A reaction chamber comprising the metal wire, e.g. the electrode described herein, can e.g. be obtained by the deposition of a metal (such as gold), combinations of metals or alloys. Several methods are known in the art for said purpose; examples include, physical vapor deposition and electroless plating. The layout is typically achieved by cutting, shadow masks, standard lithography, self assembly or other methods known to a specialist in the field.

With reference to FIG. 1, the inventive method is explained further: An enzyme (21, 22) is bound specifically to a specific target molecule (31) in the immunoassay. (22) produces a small molecule (29) which in turn interacts with the metal wire by dissolving it. This dissolution process changes the electrical conductivity and resistivity of the wire. The concentration of target molecule (31) is correlated to the change of conductivity and/or resistivity of the wire. Using this method, target molecule detection in immunoassays is possible; the method thus avoids optical systems.

In a second aspect, the invention relates to novel electrodes; these electrodes are particularly useful in the methods and kits described herein. Thus, the invention provides an electrode (1), which (a) comprises one or more pairs of connector areas (11) and one or more wires (12) connecting the connector areas (11); (b) consists of a metal selected from the group consisting of ruthenium, rhodium, palladium, silver, gold and its alloys, in particular silver, gold and its alloys; and (c) each wire (12) has a weight in the range of 10 pg-100 μg. This aspect of the invention shall be explained in further detail below:

Design of Electrode (1):

The electrode consists of at least two areas which are large enough to contact them by wires (contact areas (11)) and at least one metal wire (12). It was found particular suitable to select a specific size range for the inventive electrode to ensure appropriate measuring signals are obtained. Due to the small sizes as outlined below, the present electrodes are termed "microelectrodes" to clearly distinguish from known metal electrodes, as used e.g. in chemical synthesis.

In an advantageous embodiment, the thickness of the electrode is between 2 nm to 100 micron, preferably between 7 nm to 1 micron, most preferably between 10 nm and 100 nm. In an advantageous embodiment, the width of the electrode is between 5 nm and 100 micron, preferably between 10 nm to 20 micron, most preferably between 100 nm and 1000 nm. In an advantageous embodiment, the length (l) of the wire is up to 30 mm. Such electrodes are obtainable by using lithographic processes known from manufacturing of microchips.

Design of Wire (12):

The size of each wire is characterized by its maximum length (l) of below 30 mm and the thickness of the electrode, 1 nm to 100 micron. To provide suitable electrical signals, the weight of the wire should be in the range of 10 pg-100 μg; preferably 100 pg-10 μg, particularly preferably 0.1 ng-1 μg. By selecting a specific material and considering the above weight, length and width, the wire may be adjusted accordingly.

The geometry of the wire depends on the general layout of the reaction chamber: While a regular stripe as given in FIG. 2 can be implemented either as a separate item into a specialized container (e.g. from the cover of the specialized container downwards) or directly into the wall or bottom of the specialized container. Improved designs may be obtained from covering parts of the wire with a polymer. This concentrates the action of the metal dissolving agent on a small part of the wire (13) thereby accelerating the change in electrical properties. The invention thus also provides an electrode (1) as described herein which is coated but a contact area (13) which is un-coated. By this embodiment, the contact area is reduced and thus the electrical property measured is improved.

Materials of Electrode (1):

A broad range of materials may be used for the inventive electrodes. Suitable materials should dissolve upon exposure to a metal dissolving agent in an acceptable time upon reaction conditions, e.g. within 30 min at temperatures below 70° C. in an aqueous environment. As outlined above, suitable materials include ruthenium, rhodium, palladium, silver, osmium, iridium, gold its alloys and combinations thereof. Preferred materials are ruthenium, rhodium, palladium, silver, platinum, gold and its alloys, particularly preferred are silver and gold and its alloys; most preferred is gold. A combination of metals/alloys as outlined above includes a layered structure of metals/alloys within the inventive electrode. In one embodiment, the electrode consists of a metal which is not platinum.

Manufacturing of the electrode/wire: The manufacturing of electrodes and wires as described herein may be performed using standard techniques and standard known in the field and equipment commercially available. The methods include metal evaporation, such as electron-beam metal evaporation. Further details may be taken from the examples provided below.

In one embodiment, the metal wires are directly printed by ink jet methods onto a substrate like, glass, ceramics or polymers. Preferred metals for ink jet printing are silver and gold, which become conducting after a baking step.

In another embodiment the metal wires are produced by lithography methods, like e-beam-, light, UV- or deep UV lithography. The standard lithography process consists of the deposition of photoresist on a substrate, like glass or silicon/silicon dioxide wafers. After baking, a lithography mask with the layout of the wire and connector areas is aligned on the photoresist coated substrate and exposed to light of the corresponding wavelength. After a curing treatment, the substrate is dipped in a developer solution and areas exposed to light (negative resist) respectively areas not exposed to light (positive resist) are dissolved. By metal deposition, either sputtering or metal evaporation, the metal of choice is coated on the substrate with a predetermined thickness between 5 and 500 nm. In some cases a thin adhesive metal layer is deposited between the substrate and the metal of interest to promote adhesion. After metal deposition, the remaining resist is removed by a stripping step.

In a further embodiment, the invention provides an electrode as described herein, adapted for 2 point measurements (c.f. FIG. 2A, 2B), or 3 point measurements, or 4 point measurements (cf. FIG. 2C). In these embodiments, the connector areas (11) are adapted accordingly.

In a further embodiment, the invention provides an electrode as described herein, adapted for target molecules present in a static sample (cf. FIG. 2A) or target molecules present in a flowing sample (FIG. 28). In these embodiments, the wires (12) are adapted accordingly.

In a further embodiment, the invention provides an electrode as described herein, wherein said electrode or said one or more wires (12) are free of—or essentially free of—immobilized molecules. In this embodiment, no molecules are permanently attached (e.g. by covalent bonding, absorption, adsorption) to said wire/electrode. This embodiment is considered advantageous, as no additional manufacturing step is required. Further, without being bound to theory, it is believed that the absences of attached molecules improves the inventive method, as the aimed dissolution of the metal is not hindered.

From the above, it is apparent that the electrode as described herein may be part of a sensor. Consequently, the invention also provides in a further embodiment, a sensor comprising one or more electrodes as described herein. Depending on the set up of the kit (as described herein), the sensor may comprise (a) only one electrode; (b) two electrodes (such as a measuring electrode and a reference electrode); (c) a plurality of electrode (such as corresponding to the number of wells of an assay plate, particularly 96).

From the above, it is apparent that the sensor as described herein may be part of a measuring device. Consequently, the invention also provides in a further embodiment, a measuring device comprising one or more sensors as described herein. Additionally, other electrodes may be present in the measurement setup; e.g. to determine the temperature, electrochemical potential or concentration of molecules/ions present in the solution. The use of additional electrodes can be necessary when factors disturbing the standard procedure are present. Compared to the prior art, the present invention provides measuring devices that do not require optical systems (including lenses, light generation, light transfer, light collection, light detection, photo-multipliers, AC/DC converters, signal generation and readout electronics). Such inventive measuring devices are therefore considered less expensive and more robust. In addition, no measurement of a current, resistance or potential of a liquid sample between two separate electrodes is used, like in standard amperometric or potentiometric tests for target molecules.

In further embodiments, the invention provides the use of (a) an electrode as described herein; (b) a sensor as described herein; and (c) a measuring device as described herein in a method as described herein. It is apparent that the wire (12) will lose material when used in a method as described herein. Depending of the set up of the inventive kit and/or the inventive measuring device, the electrode is adapted for single use or for multiple use.

In further embodiments, the invention provides a kit as described herein further comprising (a) one or more electrodes as described herein or (b) one or more sensors as described herein or (c) one or more measuring devices as described herein. Consequently, the invention provides in a further embodiment an electrode as described herein, (a) adapted for single use or (b) adapted for multiple use. As the electrode will lose material upon intended use, such electrode may be considered a sacrificial electrode or a consumable electrode.

In a third aspect, the invention relates to an assay kit, particularly to an assay kit suitable for a method as described herein. Said assay kit comprises (i) a metal wire as described herein; (ii) a detection biomolecule being linked to an enzyme, and (iii) the substrate of the enzyme. The detection biomolecule, the enzyme and the substrate are described in detailed above. Preferably, the wire has a weight of at least about 10 pg or at least about 100 pg and/or a weight of up to about 1 ug, preferably up to about 10 ug, more preferably up to about 100 ug. In a preferred embodiment, the wire is made of silver or gold or its alloys.

In an advantageous embodiment, the assay kit is adapted for a one or multiple well plate test, such as a 96 well plate. Said kit can comprise at least one multiple well plate containing at least one, preferably only one, inventive wire within each well, optionally a measuring device connected to said wire, enzyme-biomolecule conjugate and substrate for said enzyme lyophilized or in buffer solutions and buffer-, wash- and blocking solutions. The plate may be precoated by the capturing biomolecule (30) and a blocking agent known to the specialist in the field. The assay can be conducted like a standard ELISA, whereby the enzyme-detection biomolecule and enzyme substrate combination contained in the kit are used. The results are e.g. evaluated using the measuring device itself or readout via a computer.

In a further advantageous embodiment, the assay kit is adapted for a test strip. Said kit comprises a least one test strip; optionally a measuring device; one or more buffer solutions and enzyme-biomolecule conjugates; capture biomolecules and enzyme substrates either as a powder, in buffer solutions or impregnated on said test strip. At least one inventive electrode is present either in the measuring device or on the test strip. The test strip can be inserted in the measurement device to start the test.

The kit can further comprise instructions for use.

To further illustrate the invention, the following examples are provided. These examples are provided with no intend to limit the scope of the invention.

EXAMPLE 1

Dissolution of Gold Through the Combined Action of an Enzyme and its Substrate

Gold was sputtered onto polystyrene discs (layer height: 50 nm) and put into microplate wells. 1 ml of 1.75 mg/ml linamarin in PBS at pH 7.4, 0.5 ml PBS and 0.09 ml of 1 Unit/ml linamarase were added to the well. The blank contained no linamarase. The absorbance of the gold layer was measured at 450 nm, as the absorbance correlates with the gold layer thickness.

TABLE 1

Normalized absorbance (450 nm) of samples from Ex. 3

| Time (min) | Blank | Sample 1 | Sample 2 |
|---|---|---|---|
| 0 | 0.995 | 1 | 0.999 |
| 10 | 0.998 | 0.99 | 0.997 |
| 50 | 0.994 | 0.889 | 0.896 |
| 100 | 0.982 | 0.666 | 0.696 |
| 200 | 0.962 | 0.257 | 0.271 |
| 300 | 0.954 | 0.068 | 0.086 |
| 400 | 0.952 | 0.023 | 0.034 |
| 700 | 0.954 | 0.002 | 0.007 |

EXAMPLE 2

Figure 3:
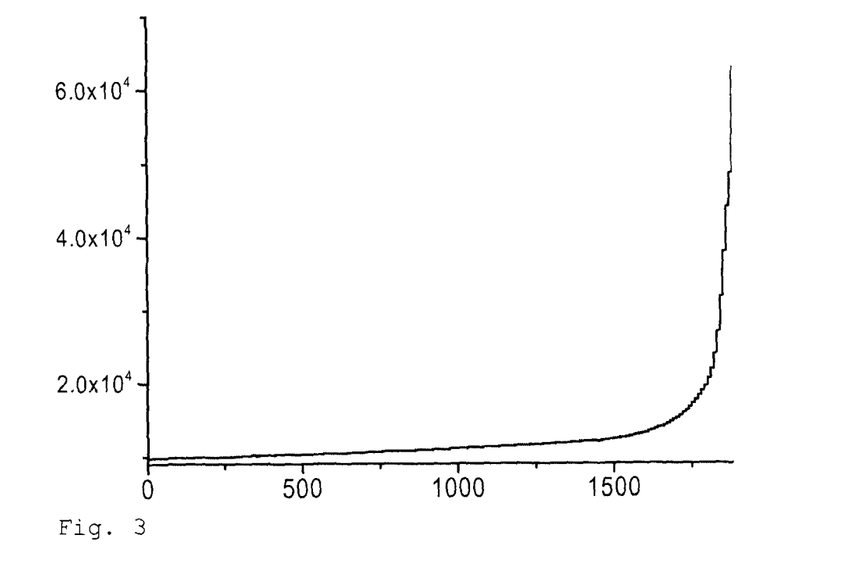
FIG. 3 shows an example of the action of linamarase produced cyanide on the gold wire within an inventive electrode (1 µU of linamarase). In this graph, the X-axis denotes the time [minutes], the Y-axis denotes the electrical resistance [Ohm].

The inventive electrode containing a gold wire (1 μm, 50 nm thick and about 3 mm long) is contacted with a solution containing 1 ppm cyanide at pH 11 and 0.1% $H_2O_2$. The response of the resistance towards the dissolution of the gold stripe due to the action of cyanide is shown in FIG. 3.

EXAMPLE 3

Figure 2:
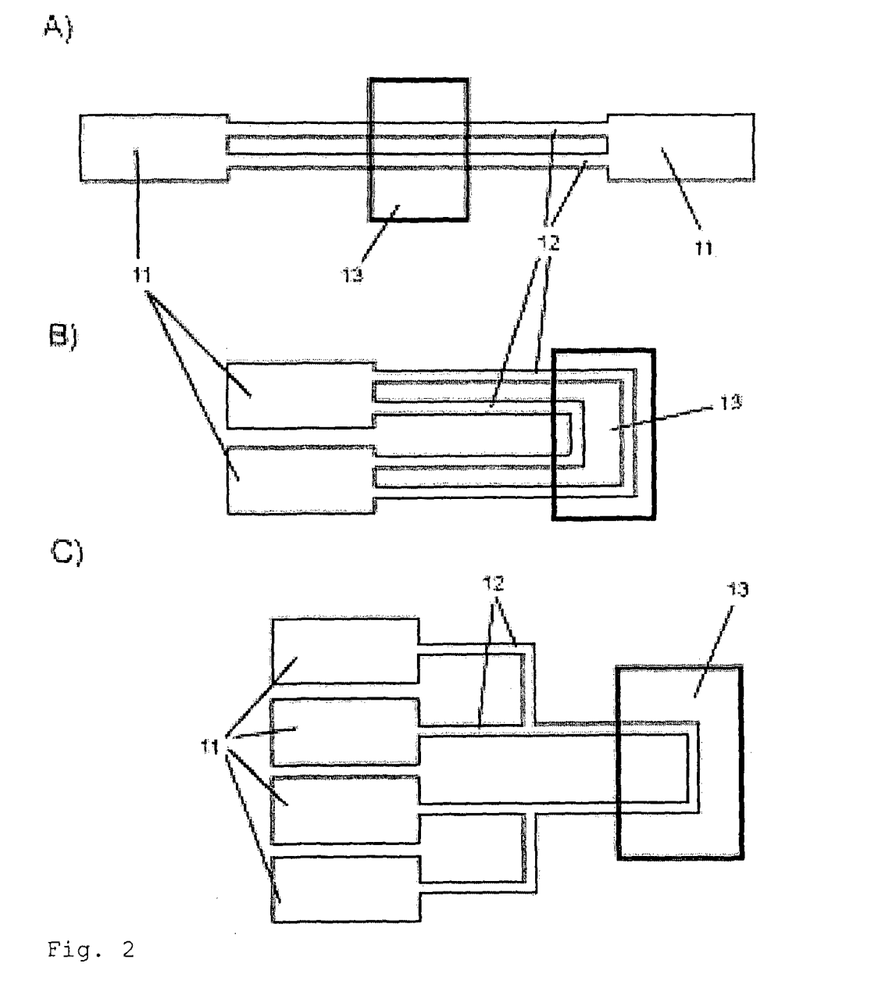
FIG. 2 shows three exemplary designs of an electrode according to the invention, identified as A), B) and C). In this figure, the references are as follows.
Figure 4:
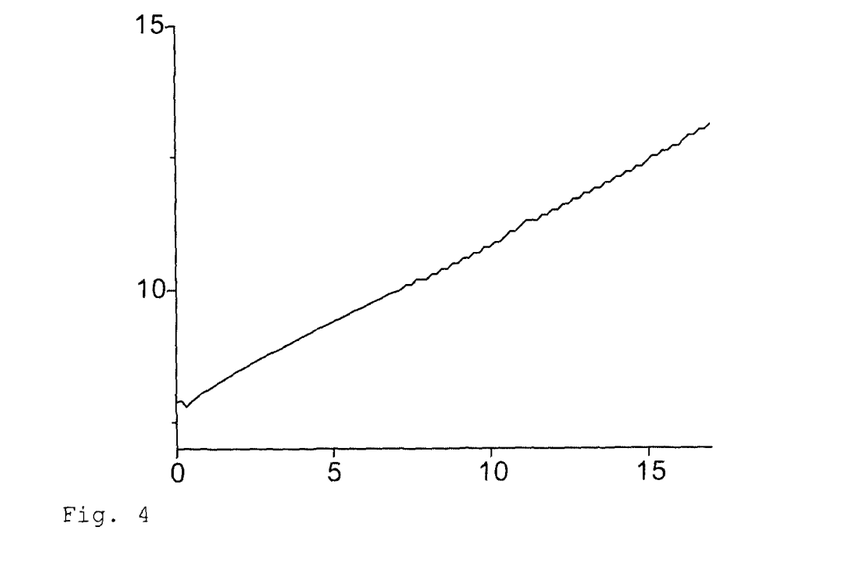
FIG. 4 shows the change of electrical resistance produced by an inventive electrode containing a gold wire upon immersion into a solution (1 ppm cyanide). In this graph, the X-axis denotes the time [minutes], the Y-axis denotes the electrical resistance [Ohm].

An inventive electrode as shown in FIG. 2 is immersed into a solution containing $1*10^{-10}$ g linamarase in 100 μl PBS at pH 7.4 and 50 μl of 2 mg/ml linamarin and 1 mg/l $Bi(NO_3)_3$ in PBS at pH 7.4 was added. The resistivity of the inventive electrode was measured by a 4 point measurement. The result is shown in FIG. 4. The resistivity of the wire increases up to a point, where the resistivity increases rapidly as the wire gets thinner and narrower.

EXAMPLE 4

A inventive electrode as shown in FIG. 2C is immersed into a solution containing defined amounts of cyanide ions in 150 μl 1 mg/l $Bi(NO_3)_3$ at pH 12. The resistivity of the inventive electrode was measured by a point measurement. In the table the slope of the resistivity in time is shown.

TABLE 2

Dependence of cyanide conc. on resistivity change in time.

| Cyanide concentration | Slope in (Ohm/10 sec) |
|---|---|
| 0 ppb | 0.06 |
| 1 ppb | 0.23 |
| 10 ppb | 0.32 |
| 100 ppb | 3.72 |
| 1000 ppb | 32.32 |

EXAMPLE 5

A standard ELISA assay was conducted and modified for electrical readout with cyanide ions dissolving a gold wire within the inventive electrode.

Functionalization of Beta-Glucosidases with Biotin:

A solution of 1 mg/ml beta-glucosidase with a molecular weight of approx. 60000 g/mol in 0.1M PBS was incubated at room temperature with NHS-Biotin reagent containing a chromophore (ChromaLink) in a molar ratio of 1 to 15 for 2 h at room temperature. Afterwards the reaction mixture was purified by size exclusion chromatography using spin down columns. Measuring the absorbance of the chromophore, yielded the molar substitution ratio (MSR). For molar ratio of 1, 5, 15 a MSR of 1 respectively 4 and 8 was obtained.

Testing the Activity of the Biotinylated Glucosidases:

96 well plates were coated with streptavidin (200 ul, 10 ug/ml in PBS pH 7.4, 10 mM), washed (3×400 ul, 0.05% Tween20 in PBS pH 7.4, 10 mM), blocked with 300 ul 1% bovine serum albumin in PBS ph 7.4 (10 mM) and washed again. Then the wells were incubated with the biotinylated glucosidases (200 ul, 1 ug/ml in PBS pH 7.4, mM) and washed afterwards. After incubation with para-nitrophenol-beta-D-glucoside (200 ul, 2.3 mM in PBS pH 6.2, 10 mM) at RT for 20 min, the absorbance at 405 nm was measured. This showed that enzymes with MSR=8 were 30% less active and enzymes with MSR=4 12% less active than enzymes with a MSR=1. Therefore the preferred substitution ratio is 1.

ELISA Assay:

A 96-well plate coated with human C-reactive protein (CRP) (2 h, 10 ug/ml in PBS pH7.4 10 mM, 200 ul) was blocked by incubation with 300 ul 1% BSA solution in PBS pH 7.4 for 30 minutes. After washing the wells with 3×400 ul 0.05% Tween 20 in PBS pH 7.4, 200 ul aqueous buffered solution with known concentration of CRP (PBS, pH 7.4, 10 mM) was incubated for 1 h in the wells. After an additional washing step, the streptavidin modified CRP detection antibody was added (200 ul, 1 ug/ml in PBS pH 7.4, 10 mM) and allowed to bind to immobilized CRP for 30 minutes in the wells. After washing the biotinylated beta-glucosidase (molar substitution ratio of biotin equal to 1) was added (200 ul, 1 ug/ml in PBS pH 7.4, mM) and allowed to bind to the immobilized streptavidin modified antibody for 30 minutes. After washing a substrate solution containing a substrate of the biotinylated enzyme was added (Substrate: Linamarin, 200 ul of 2 mM in PBS pH 6.2, 10 mM) and allowed to react with the enzyme for 10 minutes. The substrate incubation was carried out at 25° C. After addition of a 20 ul stop solution containing 0.05M sodium hydroxide, 1 mg/l bismuth nitrate and 0.1% hydrogen peroxide. At this point, the gold wire (sensor, as shown in FIG. 2C, with an initial resistance of 30 kOhm, produced by standard UV lithography process on 300 nm silicon dioxide on silicon) was inserted into the solution and the resistance was measured in a 4 point setup using a constant applied bias of 2 mV. The resistance was monitored until a steady increase is observed. After this, the slope of the resistance versus time was extracted and compared to a reference value. This leads to the corresponding concentration of CRP in the test solution. For the lowest detectable concentration of 1.3 ug/ml (limit of detection 3.9 ug/ml) the resistance changed with 230 mOhm/min. The highest tested concentration of 10 mg/ml CRP, yielded a change of 1.03 kOhm/min.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patents, and sequences cited in this disclosure are incorporated by reference in their entirety. To the extent the material incorporated by reference contradicts or is inconsistent with this specification, the specification will supersede any such material. The citation of any references herein is not an admission that such references are prior art to the present invention. Those skilled in the art will recognize, or be able to ascertain using no more than routine experimentation, many equivalents to the specific embodiments of the invention described herein. Such equivalents are intended to be encompassed by the following embodiments.

The invention claimed is:

1. A method for detecting a target molecule in a sample by means of a metal wire, said method comprising the steps of:
   a) providing a detection biomolecule interacting with the target molecule, wherein said detection biomolecule is linked to an enzyme;
   b) contacting the sample with the detection biomolecule, thereby the detection biomolecule and the target molecule interacting together;
   c) separating non-interacting and interacting detection biomolecules;
   d) adding a substrate of the enzyme;
      transforming the substrate by enzymatic catalysis into a product, said product being a reactive species dissolving metal of said metal wire, thereby altering the conductivity of the metal wire;
   e) measuring the conductivity/resistance of the metal wire, thereby detecting the target molecule;
   wherein the wire is made of a material selected from the group consisting of silver, gold and its alloys; and
   wherein the reactive species dissolving the wire is selected from among cyanide, cyanohydrin, hypochlorite, hypobromites, iodine, triiodide, and thio-cyanate.

2. The method of claim 1, wherein the target molecule is selected from the group consisting of small molecules, polypeptides, nucleic acid sequences and oligo- or polysaccharides.

3. The method of claim 1, wherein the target molecule binds to a capturing biomolecule, said capturing biomolecule being an antigen, an antibody or a complementary nucleic acid.

4. An assay kit for the method of claim 1, comprising
   (a) a metal electrode having a weight of at least 10 pg and at most 100 pg,
   (b) a detection biomolecule being linked to an enzyme, and
   (c) the substrate of the enzyme.

5. The method of claim 1, wherein the detection biomolecule is an antibody or an oligonucleotide being complementary to the target DNA or RNA.

6. The method of claim 1, wherein the enzyme is selected from the group consisting of: hydrolases, glucosidases, peroxidases, esterases, etherases, sulphur transferases, desulfohydrolases, cystein synthase, nitrilase and nitrilehydratase.

7. The method of claim 1, wherein the substrate is selected from the group consisting of cyanogenic glycosides, cyanogenic lipids, hydrogen peroxide, thiosulfate, esters or ethers of alpha hydroxynitriles, iodide, chloride, bromide, or biomolecules comprising a iodide, chloride or bromide group.

* * * * *